United States Patent [19]
Flaherty et al.

[11] Patent Number: 5,312,337
[45] Date of Patent: May 17, 1994

[54] CATHETER ATTACHMENT DEVICE

[75] Inventors: J. Christopher Flaherty, Topsfield; William J. Gorman, S. Hamilton; Paul V. Fenton, Jr.; Kelly A. Moynihan, both of Marblehead; Andrew M. Mailloux, Lawrence, all of Mass.; Thomas M. Young, Traverse City, Mich.

[73] Assignee: Strato Medical Corporation, Beverly, Mass.

[21] Appl. No.: 894,823

[22] Filed: Jun. 8, 1992

Related U.S. Application Data

[63] Continuation-in-part of Ser. No. 595,172, Oct. 10, 1990, Pat. No. 5,129,891.

[51] Int. Cl.5 .............. A61M 11/00; A61M 5/32; A61M 25/00; F16L 27/00
[52] U.S. Cl. .................... 604/93; 604/283; 604/175; 285/278; 285/280
[58] Field of Search ........... 285/238, 360, 361, 376, 285/396, 401, 402, 272, 278, 280, 177, 315, 390, 392; 604/264, 256, 280, 283, 905, 175, 93

[56] References Cited

U.S. PATENT DOCUMENTS

| | | | |
|---|---|---|---|
| 1,042,098 | 10/1912 | English | 285/278 X |
| 1,481,341 | 1/1924 | Bersted | 285/280 X |
| 2,907,591 | 10/1959 | Gulick | 285/174 |
| 3,262,718 | 7/1966 | Draught | 285/280 X |
| 3,441,296 | 4/1969 | Wilkin | 285/174 |
| 3,585,654 | 6/1971 | Jacob | 4/172.15 |
| 4,033,613 | 7/1977 | Bram | 285/184 |
| 4,273,272 | 6/1981 | Blanc | 222/464 |
| 4,296,949 | 10/1981 | Muetterties et al. | 285/18 |
| 4,325,571 | 4/1982 | Funderburg et al. | 285/177 |
| 4,625,998 | 12/1986 | Draugt et al. | 285/7 |
| 4,673,394 | 6/1987 | Fenton, Jr. et al. | 604/175 |
| 4,735,442 | 4/1988 | Bürli | 285/175 |
| 4,834,719 | 5/1989 | Arenas | 604/243 |
| 4,929,236 | 5/1990 | Sampson | 604/175 |
| 4,929,243 | 5/1990 | Koch et al. | 604/283 |
| 4,963,133 | 10/1990 | Whipple | 604/283 |
| 4,969,879 | 11/1990 | Lichte | 604/283 |
| 4,994,048 | 2/1991 | Metzger | 604/283 |
| 5,041,098 | 8/1991 | Loiterman et al. | 604/175 |
| 5,045,060 | 9/1991 | Melsky et al. | 604/93 |
| 5,178,612 | 1/1993 | Fenton, Jr. | 604/283 |

FOREIGN PATENT DOCUMENTS

| | | | |
|---|---|---|---|
| 0528494 | 3/1957 | Belgium | 285/278 |
| 782512 | 6/1935 | France | |

Primary Examiner—John D. Yasko
Assistant Examiner—Adam J. Cermak
Attorney, Agent, or Firm—Lappin & Kusmer

[57] ABSTRACT

A connector for detachably securing an end of a tube, such as a catheter, to a fluid port of a fluid transfer device, such as an implantable device, the connector having a body part which defines a coupler for coupling to a coupler receiver of the transfer device. The connector includes a sleeve which fits within the body part and defines an aperture for compressively receiving an end of the tube which has been fitted over a fluid port of the transfer device. The body part is rotatable about the sleeve to facilitate coupling of the coupler and coupler receiver. In one embodiment the sleeve has an inner diameter at one end large enough to slide freely over the tube when it is fitted over the fluid port, and the diameter decreases at an intermediate point along the length of the sleeve to provide for compressive axial movement of the tube to form an annular thickness portion of the tube where it abuts the face of the transfer device.

13 Claims, 10 Drawing Sheets

CATHETER ATTACHMENT DEVICE

This application is a continuation-in-part of U.S. patent application Ser. No. 595,172 filed Oct. 10, 1990, now U.S. Pat. No. 5,129,891, and assigned to the assignee of this application.

BACKGROUND OF THE INVENTION

The present invention generally relates to the field of tube coupling devices, and more particularly, to a device for releasably attaching an end of a tube or catheter to a port of a fluid transport device.

Flexible tubes or catheters are often used with transport devices for fluid delivery systems. For example, numerous surgical and non-surgical treatment procedures require that a catheter be placed in fluid communication with a patient's vascular system. A number of devices for this purpose are known. Both implantable treatment reservoirs, such as disclosed in U.S. Pat. No. 4,673,394, and traditional cannula devices, afford access to a patient's vascular system, using catheters attached to those devices.

Such devices may also be used for blood transfer, for example, in hemodialysis. U.S. patent application Ser. No. 354,614, assigned to the same assignee as the present application, discloses devices that are particularly adapted for this purpose. Flexible tubes are also used extra-corporeally to establish a desired fluid transport system. In the latter application, the tubes are often fit with connectors to permit flexibility in the assembly of a desired system from standardized components.

With regard to implantable vascular access devices of the prior art, catheters are typically permanently affixed to the implantable device prior to implantation. It is also known to use an implantable device which is adapted for attachment of a catheter to a chambered extension (i.e., a fluid exit or inlet port) of that device during the implantation procedure, but after the device is positioned within the patient. Typically, such catheters are adapted to be slidingly placed over a tubular port, and to be frictionally held in place.

In view of the nature of the procedures by which implantable treatment devices are surgically implanted in patients, it is necessary that the connection between a catheter and the implantable device be easily accomplished. This enables a surgeon to concentrate on the proper placement of the implantable device. Nevertheless, the friction fit and placement of the catheter has proven to require some degree of skill and patience during implantation.

Known connectors, such as, for example, a mere collar circumscribing the catheter and which fits over a tubular port projecting from the implantable device, often do not afford secure attachment. If the inner diameter of the collar does not properly correspond to the outer diameter of the catheter, either the collar will not fit over the catheter, or the collar will not generate a sufficient compressive force to secure the catheter to the port. With known assemblies, therefore, it is necessary to keep on hand a variety of connectors so that an appropriate connector can be selected and used which will specifically accommodate the particular catheter being connected.

U.S. Pat. No. 4,673,394 discloses a particularly effective arrangement for attaching a catheter to an implanted access device. That arrangement includes a twist-lockable (bayonet-type) coupler in which a pair of bayonet pins extend in opposite directions from the generally cylindrical outer surface of the coupler. The pins, together with the geometry of the coupler, may be slidingly positioned over the tubular port of the implant with a particular angular orientation, and then twisted so that the pins are captively held in place by portions of the implant which define a void region used to capture the pins.

Of course, care must be taken such that the action of twisting the bayonet-type coupler to lock the catheter to the implant does not cause the catheter to be damaged. Even with such care, torquing of the catheter should be avoided, since a twisted catheter may become partially blocked to fluid flow, or worse yet, especially in multiple lumen catheters, may become entirely blocked to fluid flow.

It is therefore an object of the present invention to provide an improved connector for securely attaching a flexible tube, such as a catheter, to a chambered extension, such as a tubular fluid exit or inlet port, of a fluid transfer assembly, such as an implantable fluid delivery device.

It is another object of the invention to provide a catheter-to-device connector which is easily installed, provides a frictional lock between the catheter and device and enables twist-lockable action between the connector and device without substantially twisting the catheter.

It is another object of this invention to provide a catheter-to-device connector which is constructed so that in the process of attaching a catheter to the device an annular thickness portion of the catheter wall is formed at the contact surface of the device to create an improved seal.

It is yet another object of this invention to provide a catheter to device connector which can provide in the attached position a positive lock retaining the connector in the attached position.

It is yet another object of the invention to provide a compression sleeve for use with a catheter connector to provide greater compressive interaction between the catheter and a fluid exit or inlet port of an implantable device.

SUMMARY OF THE INVENTION

These and other objects of the present invention are well met by the presently disclosed flexible tube connector. The connector provides easy and secure coupling of a flexible tube, such as a catheter, to a chambered extension of a fluid transfer assembly, such as a fluid exit or inlet port of an implantable fluid delivery device. The connector is configured so as to enable desired connection of the connector and assembly without causing an obstruction of the fluid flow path or damage to the tube.

The connector includes a generally cylindrical body part and a sleeve. The body part extends along a central axis; the interior of the connector body part defines a substantially cylindrical central aperture extending along the central axis, for receiving the sleeve. The sleeve exterior surface is slidably engaged to the body part interior along the central aperture. The body part engages over the sleeve, preferably in a captive manner, but remains rotatable about the central aperture and sleeve. The sleeve also defines a substantially cylindrical central aperture extending along the central axis, for compressively receiving a flexible tube (such as a catheter), which has been previously slidingly fit over an elongated fluid port (such as of an implantable device). The sleeve may, in one embodiment, be formed with a decrease in internal diameter at a point along the central axis. This decrease can provide for creeping of the tube wall as the connector is moved toward engagement, providing for a bunched wall at the interface between the body part and the fluid transfer device. The connector is provided with a locking element on the connector body (such as a T-shaped flange) and a mating receiver on the fluid transfer device (such as a generally T-shaped void region defined by a peripheral flange).

The sleeve assures compressive securing of the tube to the fluid port. In this aspect of the invention, when the sleeve is fitted over the joined tube and the fluid port, a compressive force is generated to secure the tube to the outer surface of the fluid port, while the slideable cooperation of the exterior of the sleeve and the interior of the body part permits locking interaction of the body part's locking element and a mating receiver on an implantable access device without detrimental twisting or torquing of the tube.

One aspect of the invention is adapted for use with an implantable device, such as that described in U.S. Pat. No. 4,673,394. That implantable device includes a tubular exit port extending from its periphery. The port at one end is surrounded by a generally T-shaped void region defined by a peripheral flange, which mates with the generally T-shaped connector connecting element.

In use, the catheter is fitted over the tubular fluid port of the implant and the sleeve is forced over this catheter/port conjunction to compress the resilient catheter against the port. The T-shaped coupling of the body part now is twisted about the central axis to mate that element with the T-shaped void region receiver of the implant device. This assures secure and leak-free coupling of the catheter and access port. The rotatable cooperation of the body part and sleeve assures that the body part can be turned about its central axis to effect twist-locking of the connector and implant device without torquing or twisting of the catheter. Such torquing or twisting may otherwise dangerously abuse the fluid flow path; or damage the catheter.

In a preferred embodiment, opposed wing-like elements radially project from each side of the connector body part. The wing elements are preferably adapted to be tied down to the implant to permit the coupled connector to be secured to the implant so as to prevent inadvertent decoupling. A tactile indicator may be provided to indicate to the surgeon that correct coupling of the connector and device has been made.

In a second preferred embodiment the body part also includes a retention member to securely lock the connector in the coupled position without the requirement that the wing elements be tied down.

In another preferred embodiment the fluid transfer device includes a retention member and a connector body has a wing element projecting from it to latch with the retention member thereby locking the connector in place.

The present invention may further include a compression insert, preferably tapered in cross-section, which, when inserted between the sleeve and catheter, affords further compression of the catheter against the port. This provides a greater degree of assurance that the catheter and fluid port connection will be leak-free.

BRIEF DESCRIPTION OF THE DRAWING

These and other features and advantages of the present invention will be more fully understood by reference to the following detailed description in conjunction with the attached drawing in which like reference numerals refer to like elements and in which.

DETAILED DESCRIPTION OF PREFERRED EMBODIMENTS

Figure 1:
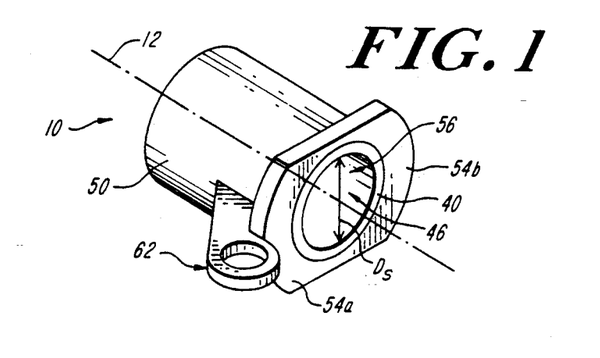
FIG. 1 is a perspective view of an embodiment of a connector embodying the present invention.

FIG. 1 is a perspective view of a connector 10 in accordance with the present invention, showing general cooperation of a cylindrical compression sleeve 40 (having an inner diameter $D_s$) fitted within a body part 50. Body part 50 is provided with extensions, such as pins or wing elements 54a, 54b, and, along with sleeve 40, generally forms a general T-shaped coupler extending along a central reference axis 12 for coupling with a generally T-shaped coupler receiver of a cooperating fluid transfer device.

Figure 2:
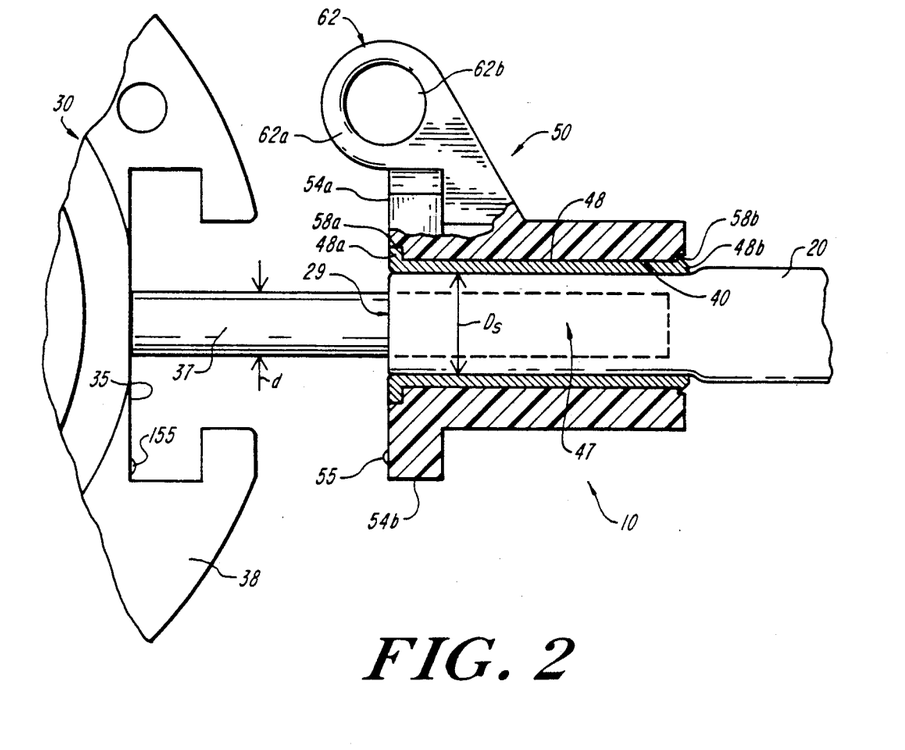
FIG. 2 is a cross-sectional view of the connector of FIG. 1 coupled over a prior art catheter fitted on a fluid port of a prior art implantable vascular access device.

FIG. 2 is a top cross-sectional view of connector 10 about to secure the proximal end 29 of a flexible vascular catheter 20 to a tubular fluid port 37 (having an outer diameter d) extending from an implantable vascular access device 30 of the type generally shown in U.S. Pat. No. 4,673,394. The distal end (not shown) of catheter 20 is positioned at a desired position in the patient's vascular system.

Figure 3:
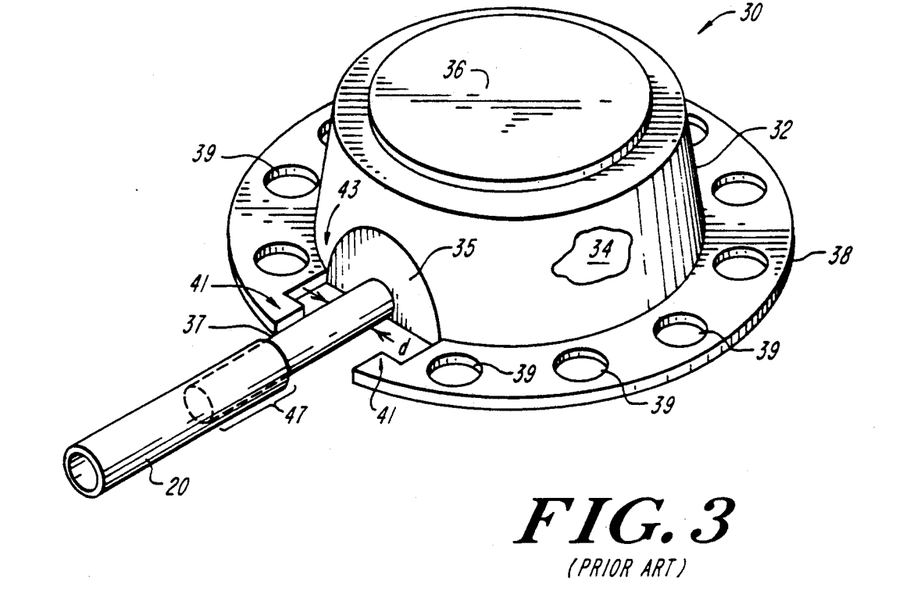
FIG. 3 is a perspective view of the prior art implantable vascular access device of FIG. 2.
Figure 4:
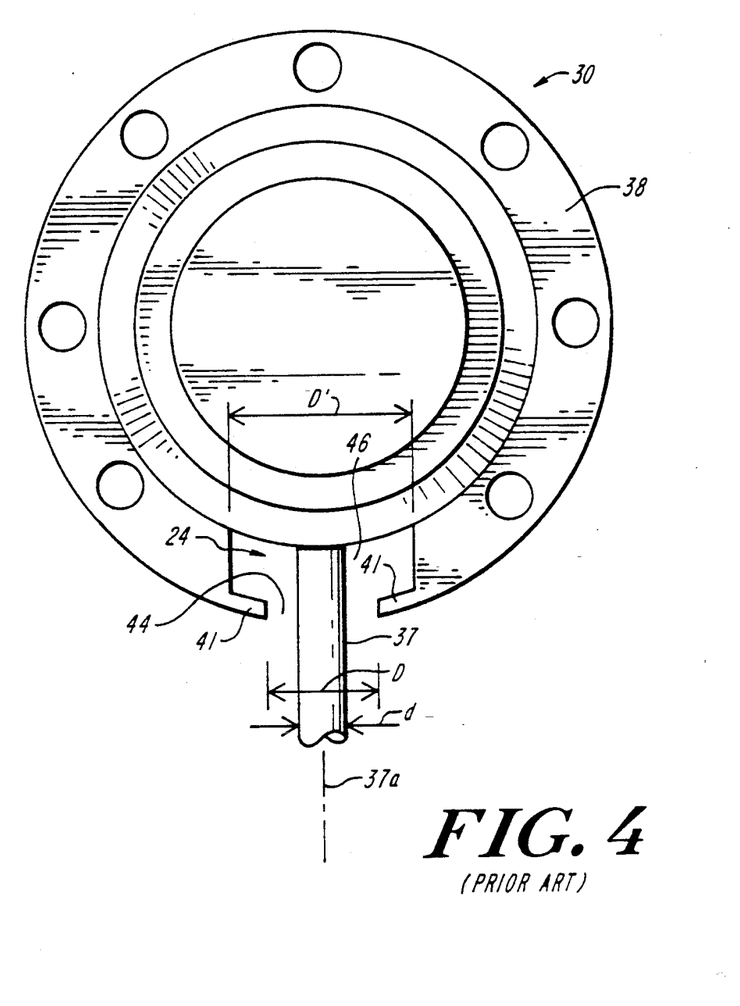
FIG. 4 is a bottom view of the prior art implantable device of FIG. 3.

In one embodiment, a cooperating fluid transfer device takes the form of an implantable vascular access device 30 as shown in the perspective view of FIG. 3 and the bottom view of FIG. 4. Device 30 preferably includes a device housing 32 which defines an internal generally cup-shaped reservoir cavity 34, e.g., for holding treatment fluids or medicine. Device housing 32 has an open face which is closed off by a cover 36. Tubular fluid flow or fluid exit (or inlet) port 37 extends out radially from wall 35 of device housing 32 along port axis 37a. The interior of port 37 is coupled directly to cavity 34.

Cover 36 is formed of a self-resealing polymer, which is preferably an elastomer such as silicone, rubber or latex, and is adapted to permit access to the reservoir cavity 34 using a hypodermic needle. Hence, in use, a hypodermic needle may be employed to puncture cover 36 to deliver a treatment fluid to reservoir cavity 34. The treatment fluid is then delivered to catheter 20 coupled to the tubular port 37 (having outer diameter d, where d is less than $D_s$) of device 30, whereby the fluid is provided to the vascular system of the patient. Device 30 may alternatively be configured to permit out-flow of body fluids, for example, blood in conjunction with a hemodialysis procedure. Device housing 32 is preferably formed of a biocompatible material, such as titanium or electro-polished 316 L stainless steel or other surgical grade steel or other hard material such as DuPont Delrin TM or Teflon TM.

A substantially planar, radially extending flange 38 circumscribes housing 32. Flange 38 includes an array of holes 39 spaced about the perimeter of housing 32, for use in suturing device 30 to a layer of the patient's tissue during the implantation procedure. Extension portions 41 of flange 38 extend on both sides of port 37. Preferably flange 38 and portions 41 define a generally T-shaped void region 24 disposed about port 37. More particularly, void region 24 comprises an axially extending portion 44 and a circumferentially extending portion 46. The axial portion 44 has a width D and the circumferential portion 46 has a width D', where D' is greater than D. Flange 38 and portions 41 and void region 24 thus form a T-shaped twist-locking receiver whose function is further set forth below.

A leak-free and secure fit is required between the resilient catheter proximal end 29 and the rigid tubular port 37. However, the difficulty of forcing catheter end 29 over tubular port 37, particularly in the restricted environment of a subcutaneous installation, requires such cooperation that the catheter end 29 slides onto port 37 with some ease. As a result, this eased coupling may not be so tight as to be leak free, or worse, may permit inadvertent disconnection.

Furthermore, the tightness of fit between the catheter and port in the past has been accompanied by a twisting of the catheter as it is forced over the port. This twisting often distorted the catheter and partly obscured the passage of fluid within the catheter. This problem is magnified when a multiple lumen catheter is employed: such catheters are more sensitive to correct alignment with a cooperating multiple lumen port, and the difficulty of obtaining correct alignment makes their secure and leak-free interconnection problematic. The present invention solves this problem.

Figure 5:
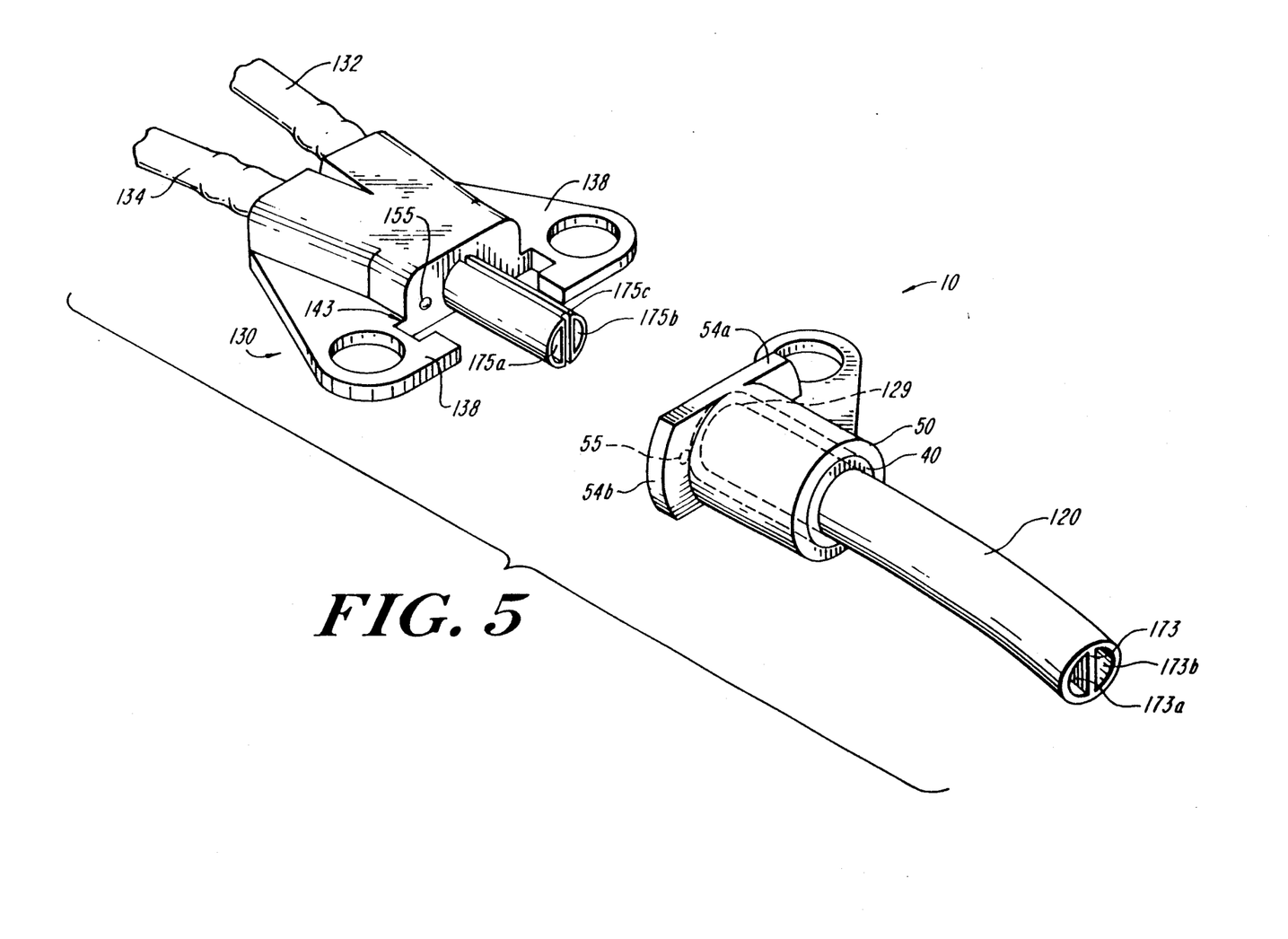
FIG. 5 is a perspective view of an alternative embodiment of the present invention adapted for coupling a dual lumen catheter to a dual lumen fluid transfer device.

By way of example, an alternative fluid transfer device 130 and associated catheters 132 and 134 are shown in FIG. 5, together with a connector 10 embodying the invention. Device 130 includes flanges 138 which define a coupler receiver 143 including a generally T-shaped region as illustrated. Device 130 is adapted to couple each of catheters 132 and 134, through one of ports 175a and 175b to a respective lumen 173a, 173b of a dual lumen catheter 120 having a proximal end 129. Catheter 120 includes an internal divider 173 which creates the two lumens 173a, 173b internal to the catheter. The two ports 175a and 175b of device 130 are separated by a gap 175c, each port being adapted to receive one of the lumens 173a, 173b of catheter 120 for transport of multiple fluids from/to a multiple lumen transfer device 130. Gap 175c is so configured as to receive catheter divider 173 as the catheter is fitted over the ports. The need for proper alignment and coupling of the respective catheter lumen and ports 175a and 175b is therefore self-evident. (It will be further appreciated, however, that the present invention applies equally well in use with a single, multiple lumen catheter and like single multiple lumen port.)

Toward these ends, for example with respect to the devices of FIGS. 2 and 5, connector device 10 of the present invention provides compression sleeve 40 to assure a leak-free and secure fit of the catheter end 29 over port 37 (FIG. 2) or end 129 over ports 175a and 175b (FIG. 5). The compression sleeve is substantially rigid relative to the substantially flexible catheter. Hence, the resilient catheter can be reasonably sized for tight but comfortable placement over port 37 (or ports 175a and 175b). The connector device 10 is first positioned so that sleeve 40 extends about end 29 (or 129) of the catheter 20 (or 120) and then this entire assembly is slidingly placed over port 37 (or ports 175a and 175b). Alternatively, the catheter can first be slidingly placed over port 37 (or ports 175a and 175b) without, or with minimal, twisting, and then compression sleeve 40 is slidingly placed over the catheter/port conjunction. The rigid sleeve supplies a higher degree of compression between the joined tube and port to assure a leak-free connection that will not easily or inadvertently disconnect.

Body part 50 defines a generally arcuate smooth inner glide surface, i.e., disposed about cylindrical central aperture 56. The outer surface of compression sleeve 40 defines a generally arcuate smooth glide surface, i.e., an exterior generally cylindrical outer contour 48 configured to cooperate with the body part central aperture 56. Sleeve 40 further defines a generally arcuate smooth-walled orifice, i.e., a generally cylindrical central aperture 46 for compressive receipt of catheter 20. Aperture 46 is of an internal diameter which causes compression of the catheter as the sleeve is slid over the surface of the catheter up to and over the catheter/port conjunction 47, as enabled by the resilient character of the catheter material (typically a plastic or elastomer).

As seen in FIGS. 1, 2, and 5, body part 50 at its central aperture 56 is fitted over compression sleeve 40 in a closely cooperating manner, thus capturing sleeve 40. However, since sleeve 40 compressively secures the proximal end 29 of catheter 20 to port 37, the sleeve essentially is fixed in the axial direction relative to the catheter. Therefore, body part 50 at its central aperture 56 must slidingly engage the outer surface 48 of sleeve 40 so that it can be twisted into locking cooperation at receiver 43 of device 30 without causing the sleeve and catheter to be twisted. Hence, it is intended that body part 50, as so mounted on sleeve 40, may be freely rotated about the relatively fixed sleeve.

Figure 6:
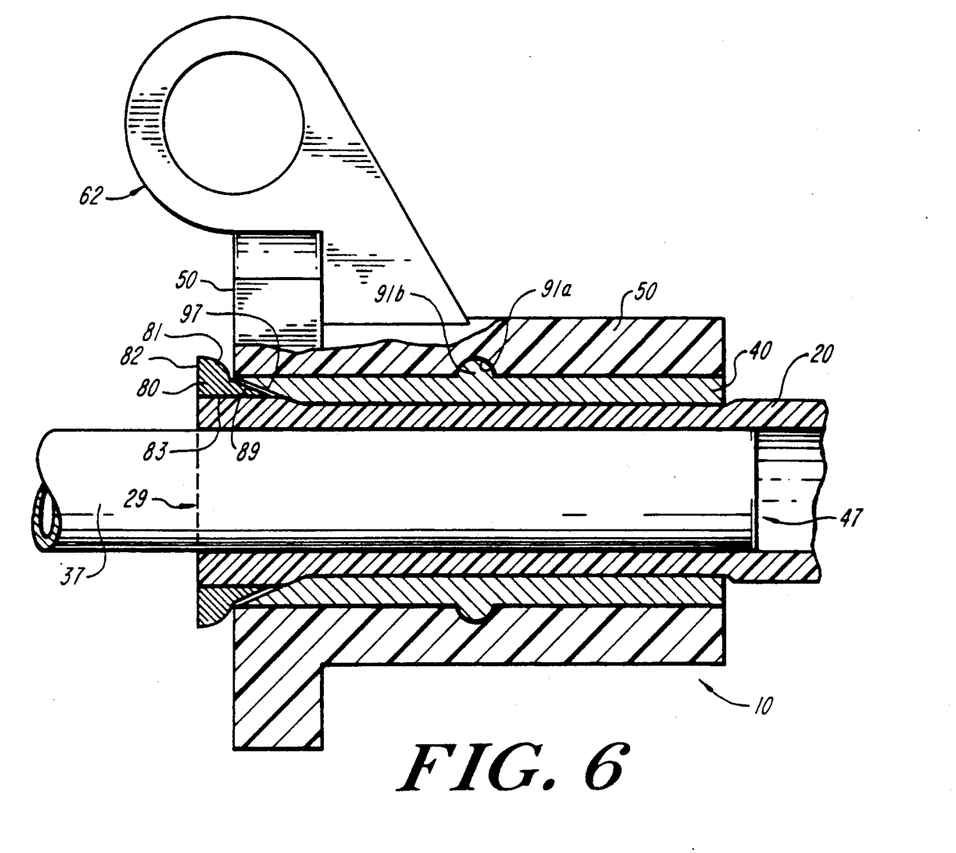
FIG. 6 is a cross-sectional view of an alternative embodiment of the invention installed over a catheter fitted over a fluid access port, but before being mated with a cooperating twist-locking receiver of a fluid transfer device.

In a preferred embodiment, body part 50 includes inset grooves 58a, 58b, and sleeve 40 includes raised flanges 48a, 48b, whereby body part 50 is installed over sleeve 40 with flanges 48a, 48b mating with grooves 58a, 58b, respectively. Now, when connector 10 is being mated with and locked into device 30, sleeve 40 is prevented from slipping away from its location over catheter 20 and catheter/port conjunction 47, while body part 50 can still be rotated about sleeve 40 during such mating. This groove/flange combination permits body part 50 to be forced over sleeve 40 after the latter has been fitted into its desired compression location over the catheter/port conjunction 47. In an alternative embodiment of connector 10, an example of which is shown in FIG. 6, only a single groove 91a and single flange 91b are provided for interlocking of body part 50 and sleeve 40. The locations of the flanges on sleeve 40 and grooves on part 50 could be reversed in yet other embodiments. Still other variations by which the sleeve 40 is captively held by body part 50 are also within the scope of the present invention.

In any event, it now will be appreciated that the relatively non-torqueable interaction of sleeve 40 and catheter/port conjunction 47 is unaffected when body part 50 is torqued to lock bayonet flanges 54a, 54b into the cooperating receiver 43 of device 30. Thus connector 10 can tightly secure catheter 20 (120) to port 37 (or ports 175a and 175b) of device 30 (130) against unwanted leakage or disconnection, and the entire connection is secured against unwanted disconnection by means of the T-shaped lock mechanism, without unwanted twisting or torquing of the catheter.

It should be understood, however, that in the context of the invention, "T-shaped" refers to any reasonable shape having a width on the perimeter of the flange 38 which is smaller than the width at the end of the void region 24 which is distal to the flange perimeter. An alternate example of such an opening would be a dovetail-shaped opening. Furthermore, it will now be appreciated that while other frictional or threaded coupling of connector 10 and device 30 is also within the scope of the present invention, a preferred T-shaped interconnection is shown and described herein.

An optional feature of the invention, as shown in FIG. 2 or 5, includes a confirmation mechanism for indication of correct coupling of connector 10 and the fluid delivery device. The mechanism may include a contact spot or protrusion 55 on connector body part 50 and a cooperating contact spot or lip 155 of the flange of the fluid delivery device. In this manner, a "tactile" or "click"-type indication of correct placement can be felt by the surgeon as the body part wing elements 54a, 54b are properly seated in the receiver of the fluid delivery device. Hence it will be appreciated that contact devices 55, 155 are designed to interact only when the T-shaped connector is properly locked in secure and mating cooperation in the T-shaped receiver of the delivery device.

In addition to the foregoing, a securing device 62 is provided on connector 10 to prevent inadvertent detachment of the connector from the delivery device. Securing device 62 may include a flange 62a which is an extension of body part 50. Flange 62a internally defines a tie down hole 62b. Tie down hole 62b permits suturing the body part perhaps to one of the plurality of holes 39 in flange 38 of device 30, for example, after connector 10 is properly connected to device 30.

It will now be appreciated that proper installation of sleeve 40 over catheter/port conjunction 47 requires selection of a sleeve with an inner diameter greater than the outer diameter of the port and less than the outer diameter of the catheter after the catheter is installed on tube 37. This normally assures adequate compression of the catheter.

Figure 7:
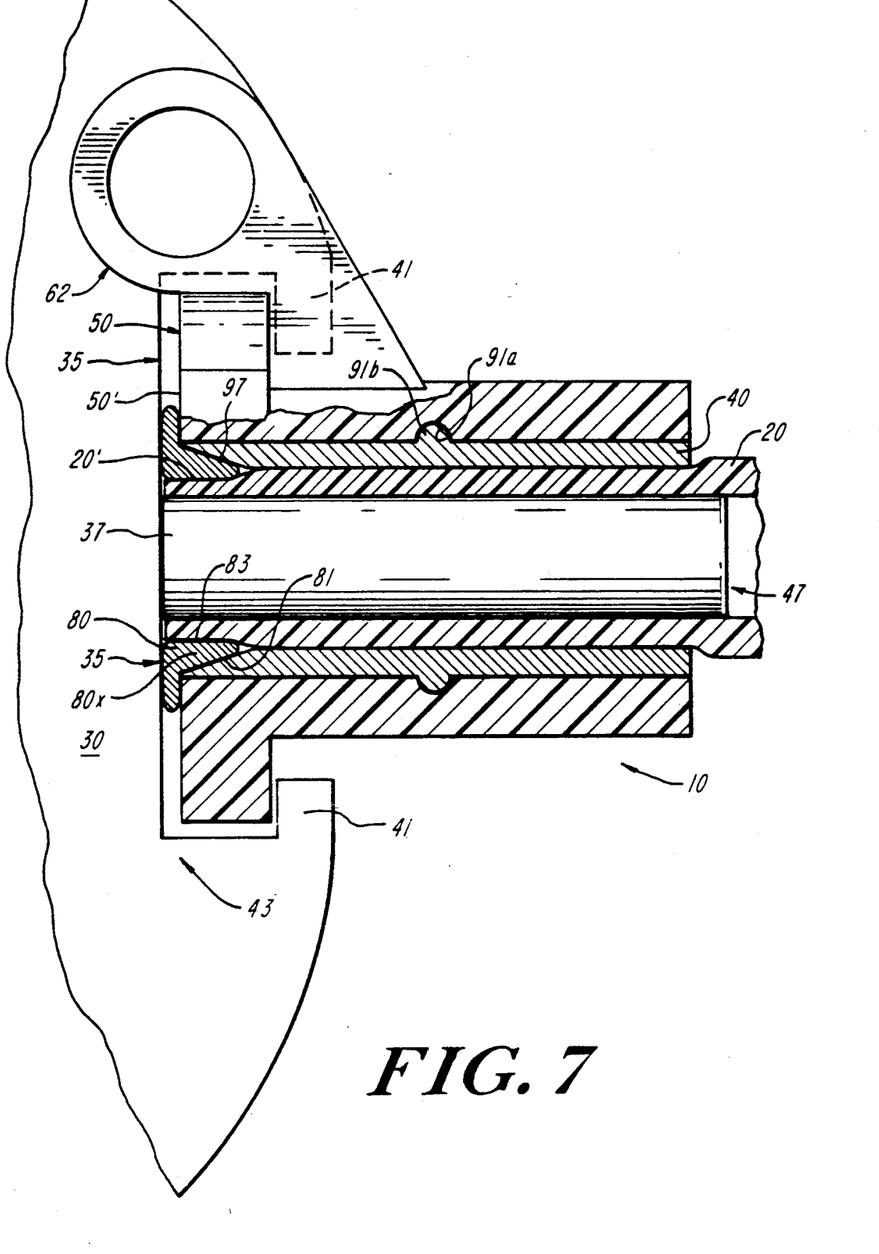
FIG. 7 is a cross-sectional view of the connector embodiment of FIG. 6 and a partial view of a fluid transfer device after the connector is mated with the twist-locking receiver of the fluid transfer device.

Notwithstanding the foregoing, further assurance of leak-free sealing at catheter/port conjunction 47 may be desired. Hence, as shown in FIG. 6, an insert 80 provides for tight coupling of the catheter/port conjunction 47. In one embodiment, insert 80 is a generally cylindrical sleeve, which in cross-section, as shown in FIG. 6, is generally wedge-shaped, and is formed from a material which is compressible between device 30 and connector 10. The insert defines an outer surface 81, an abutment surface 82, an inner surface 83, and an insertion end 89. In this embodiment, sleeve 40 is preferably provided with an inclined edge 97 which defines a tapered annular entryway for receipt of cooperatively tapered surface 81 of insert 80. In this manner, as connector 10 is locked into the twist-locking receiver 43 of device 30 the inclined edge 97 of the sleeve annular entryway compresses the insert and forces the abutment surface 82 of the insert against wall 35 of device 30, as well as around and into catheter 20, as shown in FIG. 7. Hence, insert 80 provides an extra degree of leak-free compressive sealing between catheter 20 and device 30.

In use of insert 80, preferably connector 10 is first placed over catheter 20 to overlie the catheter end 29. Then the compressible insert 80 is placed over end 29 of catheter 20. Now insert 80 and catheter 20 together with connector 10 (sleeve 40 and body part 50) are slid over port 37, with the catheter end 29 extending up toward wall 35 of device 30. The body part 50 of connector 10 is then twist-lock coupled with device 30. The action of forcing connector 10 into locked interconnection with device 30 forces compression surfaces 81, 83 between sleeve 40 and catheter 20 and forces a portion of insert 80 between wall 35 and faces 50' of body part 50 and 20' of catheter 20 to further seal the catheter's connection to device 30.

In an alternative embodiment, insert 80 may be formed as a split ring of a material similar to that of sleeve 40, having an inner diameter greater than the catheter inner diameter and less than the catheter outer diameter. The split face 80x of a split insert 80 is shown in FIG. 7.

Because device 30 is intended to be sutured directly to the patient, a high degree of maneuverability of device 30 and accessibility of suture holes 39 is desired to facilitate the surgical process of implantation. Additionally, because device 30 connects directly, via catheter 20, to the patient's vascular system, the integrity of the connection between the catheter and the device must be assured. Moreover, in order to reduce risk of harm to the patient, it is preferred that the catheter be moved minimally during and after placement of the catheter distal end within the vascular system.

It is therefore desirable, in practice of the invention, to first position and affix device 30 to the patient, then insert the distal end of the catheter to the desired patient location, then size the length of the catheter 20 by cutting its proximal end 29, and then frictionally couple the catheter proximal end 29 over tubular port 37 of device 30. Sleeve 40 is forced over the catheter/port conjunction 47, and then catheter 20 is secured to device 30 by a T-shaped coupler, formed by body part 50 mounted on sleeve 40, and T-shaped receiver 43 of device 30. The tactile aid of the confirmation mechanism (devices 55 and 155) signals correct and complete connection of connector 10 and device 30. Preferably, connector 10 is secured in its coupled cooperation with device 30 by suturing the body part securing device 62 (at securing hole 62b) to a hole 39 of flange 38.

The sleeve and body part need not be formed from biocompatible material if not to be implanted. They may be formed of DuPont Delrin TM (acetal resin), thermoplastic, metal (such as titanium), DuPont Teflon TM (polytetrafluoroethylene), or a mixture of nylon and polyethylene, as their use may dictate. The compression seal, for example, may be a split ring formed of the above materials or, as a soft compressible ring, of silicone, polyurethane, butyl rubber, or ethylene propylene.

Figure 8:
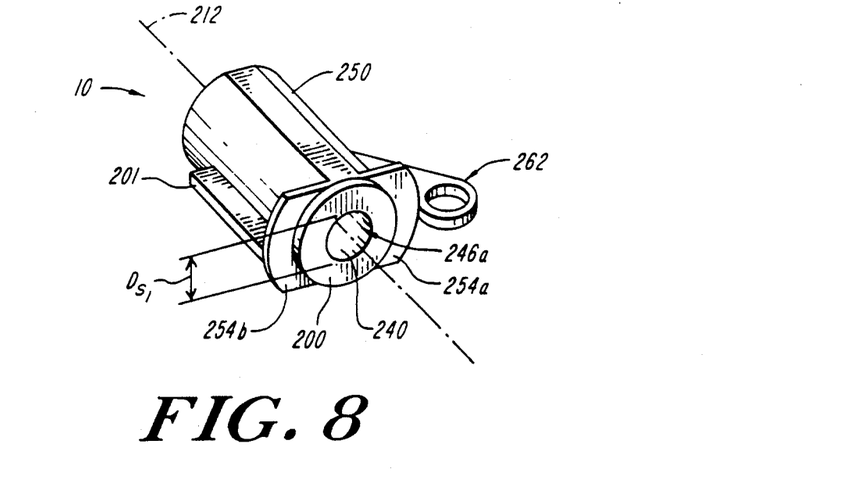
FIG. 8 is a perspective view of an additional embodiment of the invention.
Figure 9:
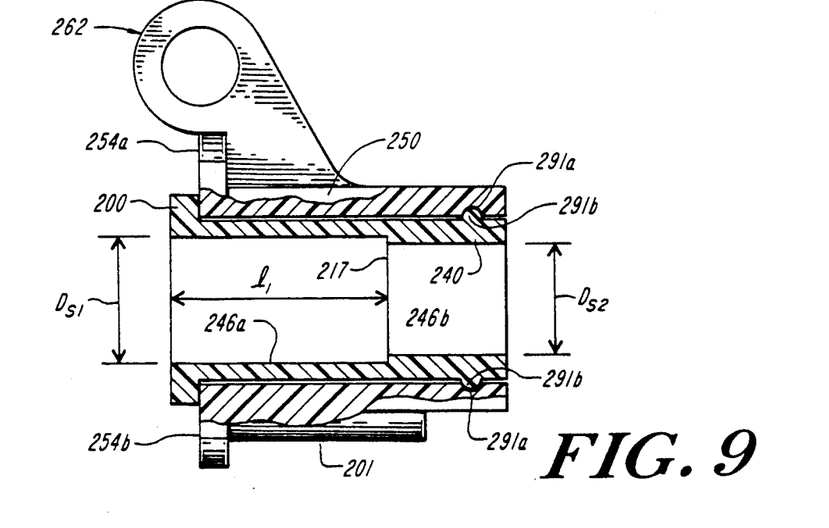
FIG. 9 is a cross-sectional view of the embodiment of FIG. 8.
Figure 12:
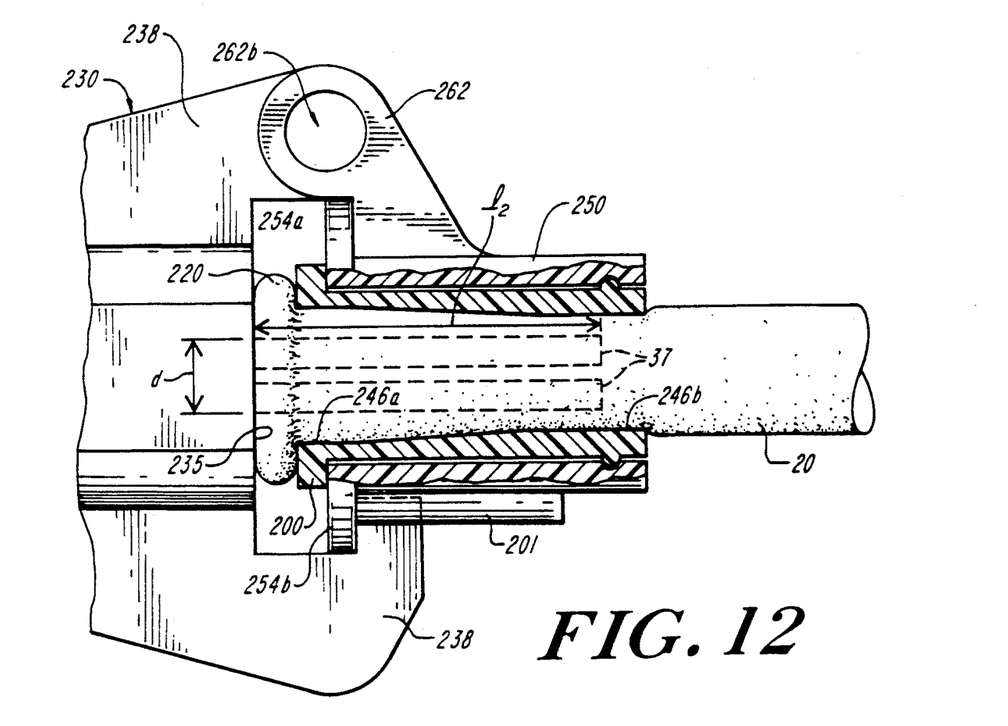
FIG. 12 is a cross-sectional view of the connector embodiment of FIG. 10 installed over a catheter fitted over a fluid access port after being mated with a cooperating twist-locking receiver of a fluid transfer device.

FIGS. 8 and 9 illustrate an alternative embodiment of connector 10. The connector 10 includes the outer body part 250 extending along a central reference axis 212 and within which is inserted compression sleeve 240 generally formed with similar features to those of the embodiments illustrated in FIGS. 1 through 5. In the embodiment of FIGS. 8 and 9, the compression sleeve 240 is formed with an outer annular flange face 200 and a rib 291b extending around the sleeve circumference. The body piece 250 includes a groove 291a positioned to receive the rib 291b when the sleeve has been inserted into a position where the flange 200 is in contact with the face of the body part 250. With this arrangement the sleeve is retained within the body part 250 by the action of rib 291b engaging the groove 291a while the flange face 200 abuts the body part 250. This allows for rotational movement of the sleeve within the body part while not allowing for any significant axial movement. Of specific note is the fact that the sleeve 240 of FIG. 9 is not formed having a single inner diameter bore, but rather the inner diameter of the sleeve in the region 246a, immediately adjacent the flange 200, has a diameter $D_{s1}$ up to point 217, where the inner diameter in the region 246b has a step decrease to a smaller bore having a diameter $D_{s2}$. The diameter $D_{s1}$ is selected to be about equal to the expected diameter d of the fluid transfer device tubular extension 37 plus twice the thickness t of the catheter 20 wall when the catheter has been stretched to fit over the tubular extension of the fluid transfer device. Diameter $D_{s1}$ can be either an easily sliding fit or a slightly compressive fit. The diameter $D_{s2}$ is less than $D_{s1}$. The length $l_1$ from the face flange 200 to the point of decreased diameter 217 is less than the expected length $l_2$ of the tubular extension 37 (FIG. 12).

Figure 13A:
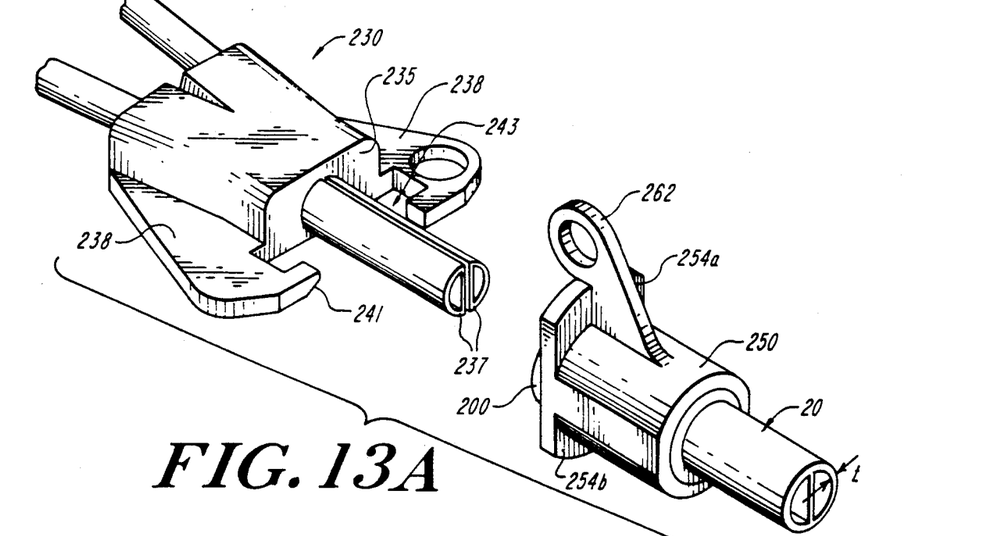
FIGS. 13A through 13C illustrate the process of moving of the connector of FIG. 12 into a locked relationship with the fluid transfer device.
Figure 13B:
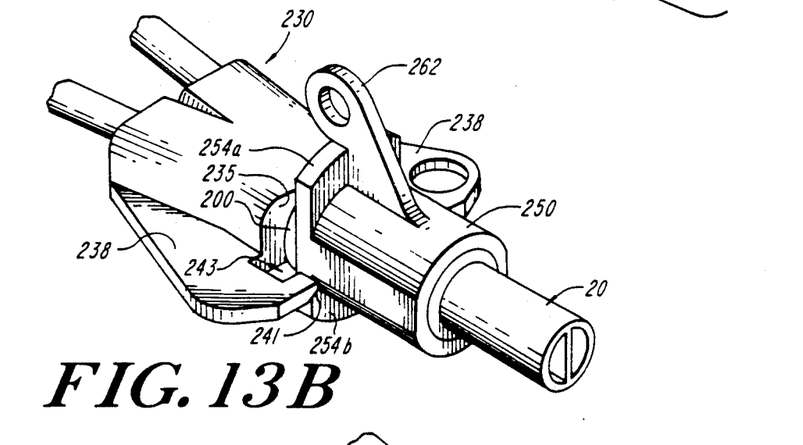
Figure 13C:
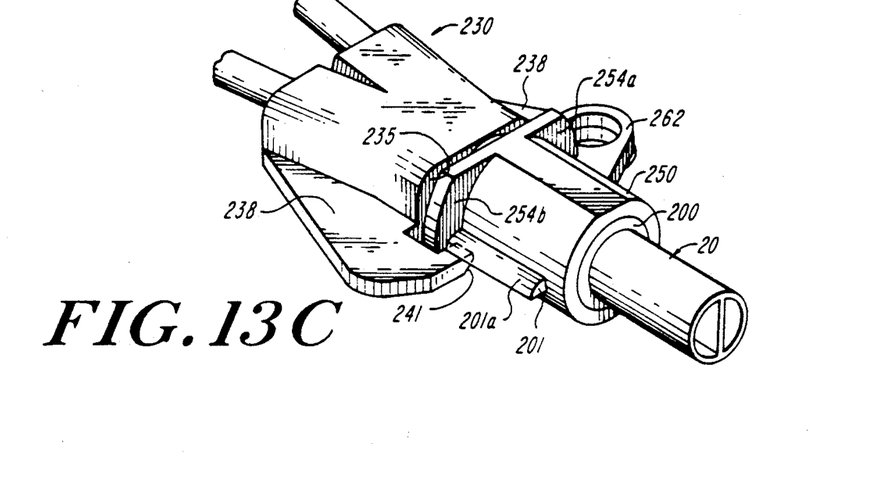

The rigid body part 250 includes wing elements 254a and 254b forming a front flange on the body part to be rotated into an interlocking relationship with the void region of the transfer device as illustrated in FIGS. 13A through 13C. In addition, a securing element 262 attached to wing elements 254a, is approximately centered on the arcuate edge of wing elements 254a, and generally is in abutting relationship with the rear face of that wing. Securing element 262 provides a convenient lever for rotating the body part 250 to engage the wings with the fluid transfer device voids for interlocking the body part and the fluid transfer device together, as well as a tie down hole 262b for suturing the body part to the fluid transfer device. On the opposite side of the body 250, located at approximately 180°, with respect to the securing element 262 is a retention member 201. This extends out from the body part radially a short distance (less than the wing element 254b on the corresponding side) and has a thickness approximately the same as that of the securing element 262. This retention element serves the function of retaining the body part 250 in its engaged locked in, position with respect to the transfer device, after the body part 250 has been rotated into engagement. The retention member 201 may be formed with a generally quarter round cross section to interact with the beveled lower surface 241 of the receiver extension portion 41, allowing the retention member 201 to slide readily by this portion 41, under clockwise rotation and once past, the flat edge of the retention element 201 provides a positive lock preventing inadvertent body part rotation. The details of this operation will be discussed below.

Figure 10:
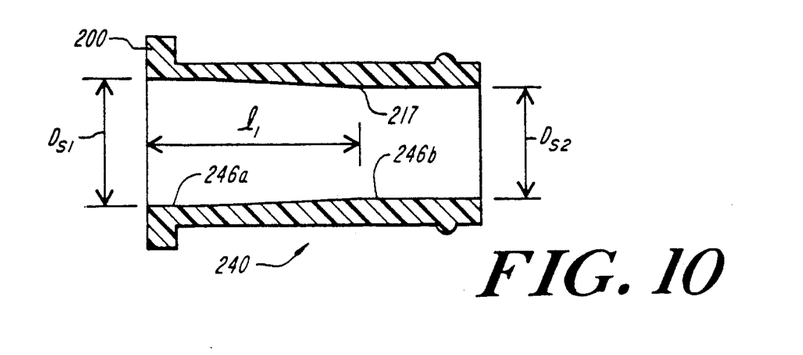
FIG. 10 is a cross-sectional view of an embodiment of the invention similar to that of FIG. 8 but with a different sleeve configuration.

In FIG. 10 there is shown an alternative version of the sleeve 240 of FIGS. 8 and 9. In the version of FIG. 10, however, rather than having a step change at the beginning of the decreased inner diameter, as is the case in FIGS. 8 and 9, the inner diameter of the sleeve 240 at the region 246a near the end of the sleeve 240 near the annular face 200, has a diameter $D_{s1}$ and tapers inwardly from that point continuously until it reaches intermediate point 217 at which the point the inner diameter in the region 246b has decreased to the value $D_{s2}$. In all other respects the version shown in FIG. 10 is the same as that shown in FIGS. 8 and 9.

Figure 11:
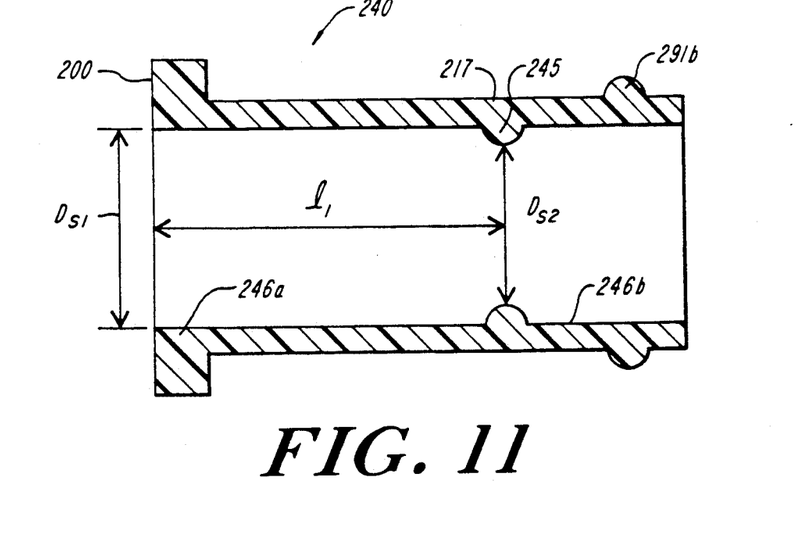
FIG. 11 is a cross-sectional view of another sleeve configuration suitable for use in the general configuration of FIG. 8.

FIG. 11 shows an alternative sleeve configuration. In this sleeve the reduction from diameter $D_{s1}$ to diameter $D_{s2}$ is achieved by an internal circumferential rib 245 positioned at point 217, and extending inwardly from the interior wall of the sleeve. The rib 245 may be continuous or may be formed of discrete separate segments.

The purpose of the decreasing inner diameters in FIGS. 8, 9, 10 and 11 is to improve the sealing at the face of the transfer assembly when the connector 10 is engaged therewith. In the process of sliding the sleeve 240 over the tubular extension 37 of the transfer assembly, when the decreased portion of the sleeve bore reaches that portion of the catheter 20 which is now fitted over the tubular extension 37, it does not continue to slide as before, but rather, because of the decrease in diameter, engages the wall of the catheter 20 closely enough to move it forward toward the abutting contact area of the transfer assembly. As illustrated most completely in FIG. 12, this causes a portion 220 of the catheter wall 20 to be bunched up and compressed between the annular face flange 200 of the sleeve 240 and the contact face 235 of a fluid transfer device 230 (similar to transfer device 130 shown in FIG. 5), resulting in the formation of an annular compressed ring 220 of the catheter wall thereby establishing a firm seal at that contact face. In order for this to work properly the length $l_1$ between the face of the annular flange 200 and the point of narrowed diameter 217 must be less than the length $l_2$ of the tubular extension 37, with the difference in this length controlling the amount of catheter material available to be compressed into the annular ring 220.

As above mentioned, another feature of this embodiment is the inclusion of a retention member 201 on the body part 250. The radial extension of the retention member 201 from body part 250 is less than the radial extension of the adjacent wing element 254b and has a ramp shaped surface 201a. Accordingly, as illustrated in FIG. 13A through FIG. 13C, when the connector is rotated into engagement, with the elements defining the void regions of receiver 243 of the fluid transfer device 230, this retention member 201 can be forced past the projection portion 241 of the flange 238 of the transfer device such that it snaps into a position on the same face of the flange 238 as securing member 262 occupies with respect to the other portion 241 of the transfer device flange 238. This provides that, when in the engaged position, the connector 10 cannot be rotated out of the engaged position without the specific effort of passing this retention member 201 back past that flange portion 41.

FIGS. 14, 15, 15B, 16A, 16B, 17A, and 17B illustrate an embodiment in which a retention element 360 for locking the connector body 350 to the vascular implantable access device 330 is located on the wall 332 of the implantable device. The retention element 360 interlocks with a wing element 362 on the connector body when the connector is in the engaged position. Thus, a seal is established between catheter the 320 and the contact face 335 of device 330. Additionally, device 330 has a cover 336.

Figure 14:
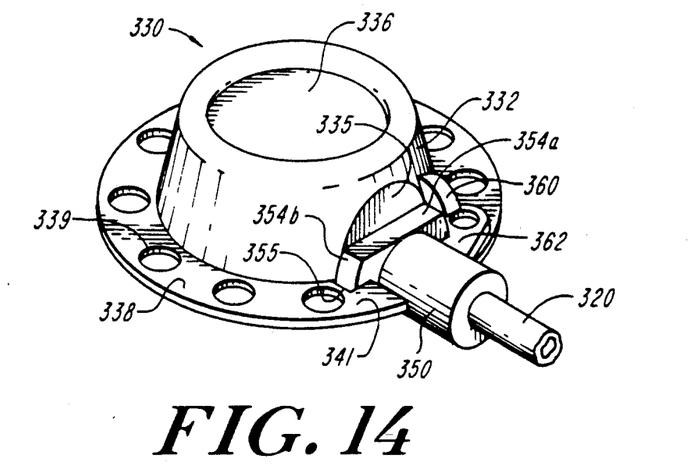
FIG. 14 is a perspective view of an implantable vascular access device having a locking retention member and including a connector locked into place.

In FIG. 14 an implantable vascular access device 330 generally as shown in FIG. 3 is shown in an interlocked position with connector body 350. Flange 338 of device 330 includes an array of holes 339 for use in suturing device 330 to a layer of the patient's tissue. A ramp shaped retention element 360 is positioned on the wall 332 of the device 330. In the engaged position, as shown, the wing element 362 of connector body 350 has been rotated past this retention element 360 and snapped into place in a horizontal position. This interlocks the connector 350 and the implantable device 330 to maintain the connector in the engaged position.

Figure 15A:
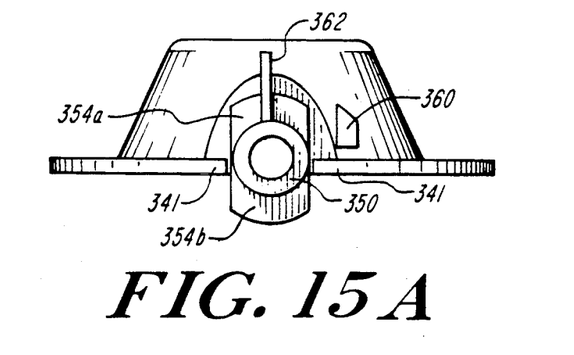
FIGS. 15A, 15B, 16A, 16B, 17A and 17B illustrate the front and side views of an implantable device as in FIG. 14 together with a connector in a sequence of steps for locking the body part to the implantable device.
Figure 15B:
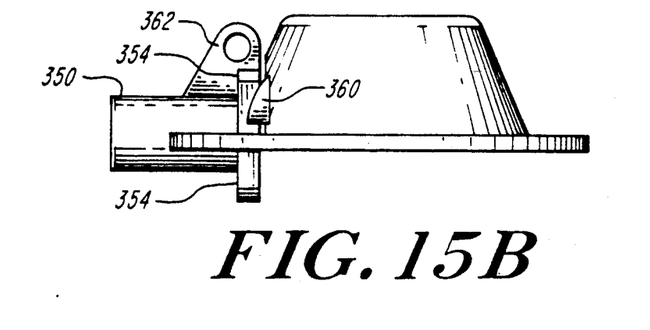

The locking sequence is illustrated in FIGS. 15A, 15B, 16A, 16B, 17A and 17B. As shown in FIGS. 15A and 15B, in step 1 the connector body part is pushed over the tubular port (not shown) of the implantable device with wing element 362 in a vertical position.

Figure 16A:
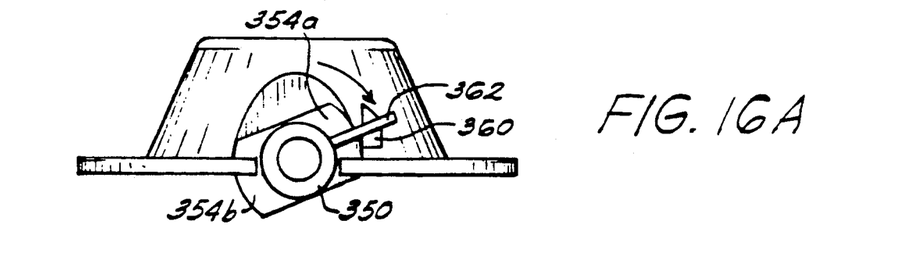
Figure 16B:
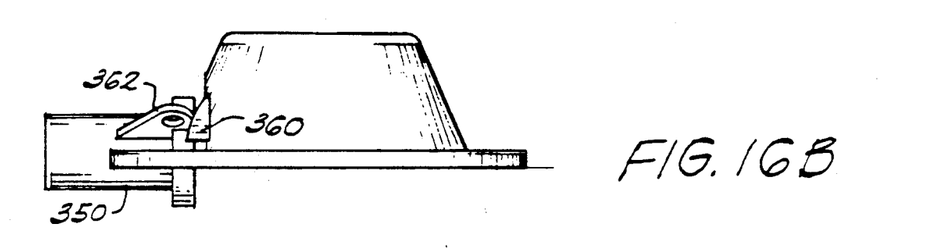

As shown in FIGS. 16A and 16B the wing element 362 is rotated clockwise to engage the ramp face of retention member 360, thereby also rotating flange 354b into the T-shaped slot 355 formed by the portions 341 of flange 338.

Figure 17A:
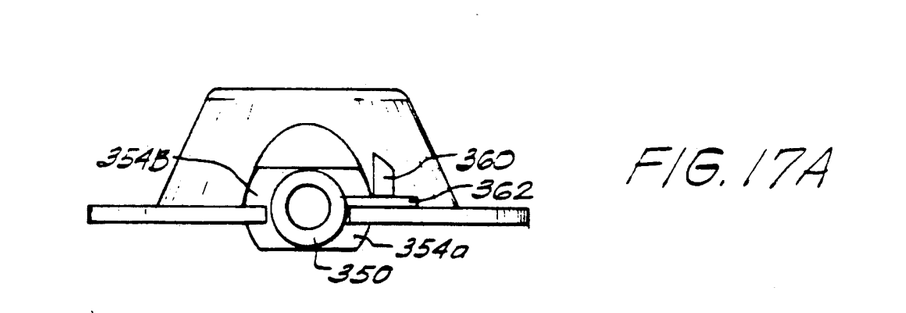
Figure 17B:
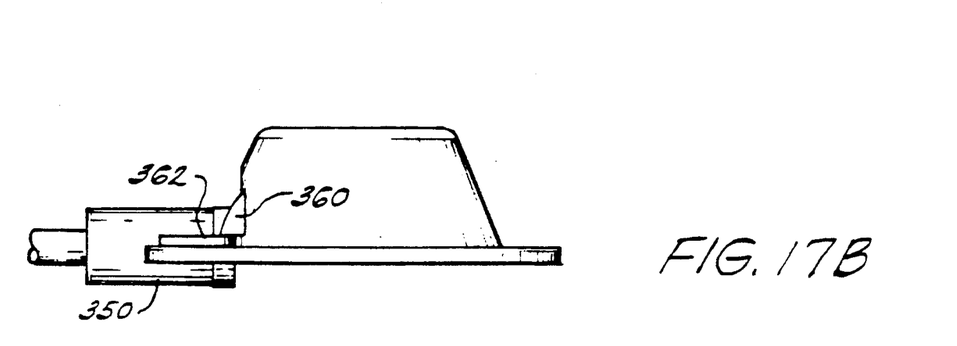

Finally, in FIGS. 17A and 17B, the body 350 of the connector is fully rotated, moving wing element 362 beyond the ramp edge of retention element 360, locking the connector body 350 to the implantable device 330, with flanges 354a and 354b held in the T-shaped slot 355.

It will be understood that the above description pertains to only several embodiments of the present invention. That is, the description is provided by way of illustration and not by way of limitation. For example, while the port and catheter are described and shown having particular diameters, connoting a circular cross-section, an oval or other non-circular cross-section is equally within the scope and teaching of the present invention. Therefore, for ease of description, the term diameter used in this document will also be understood to connote an analogous cross-sectional dimension of non-circular cross-section parts. Nevertheless, the scope of the invention is to be defined according to the following claims.

What is claimed is:

1. Connector apparatus for coupling an end of a resilient tube about the exterior of a tubular extension of a fluid transfer device, said tube having a nominal inner diameter d' and having a wall thickness t when positioned about the exterior of said tubular extension, said extension extending along a port axis and having an outer diameter d, and a length at least equal to $l_2$, where d is greater than or equal to d', said connector apparatus comprising:

A. a rigid tubular sleeve having an interior wall and extending along a reference axis from a first end to a second end, said sleeve having a first inner diameter $D_{s1}$ at said first end, where $D_{s1}$ is equal to at least about $d + 2t$, and a second inner diameter $D_{s2}$ at an intermediate point a distance $l_1$ from said first end, where $l_1$ is less than or equal to $l_2$ along said reference axis between said first and second end, where $D_{s2}$ is less than $D_{s1}$ and greater than d, and B. a rigid body part disposed about said tubular sleeve and associated capture means for capturing said sleeve within said body part, whereby said sleeve is freely rotatable about said reference axis with respect to said body part, wherein said body part further includes twist lock means at said first end, responsive to coaxial alignment of said port axis and said reference axis and to subsequent rotation of said body part about said reference axis and said port axis, for selectively engaging said body part to said fluid transfer device having said tubular extension, when said sleeve is coaxial with and positioned about said tubular extension.

2. A connector apparatus in accordance with claim 1 wherein said sleeve first end has an abutment face for abutting against said fluid transfer device.

3. A connector apparatus in accordance with claim 2 wherein the difference between $l_1$ and $l_2$ is such that said tube is compressed about said tubular extension about said tubular extension to form an annular thickened portion of said tube between said abutment face and said fluid transfer device when said body part is selectively engaged to said fluid transfer device.

4. A connector apparatus in accordance with claim 1 wherein said decreased inner diameter $D_{s2}$ occurs as a discrete step in the inner diameter of said tubular sleeve.

5. A connector apparatus in accordance with claim 1 wherein the inner diameter of said tubular sleeve decreases continuously from a value $D_{s1}$ near said first end to a value $D_{s2}$ at said intermediate point.

6. A connector apparatus in accordance with claim 1 wherein said decreased diameter is achieved by a circumferential rib extending inwardly from said interior wall of said sleeve.

7. A connector apparatus in accordance with claim 6 wherein said sleeve is generally cylindrical and said body part is formed with a generally cylindrical axial opening therethrough, said tubular sleeve having an outer diameter and said body part having an inner diameter such as to allow said tubular sleeve to have a sliding fit within said body part.

8. A connector apparatus in accordance with claim 1 wherein said capture means comprises, an annular flange on said sleeve at said first end extending radially beyond the outer diameter of said sleeve, a circumferential rib extending radially outward from said tubular sleeve at an axial position between said first end and said second end, and a circumferential groove in said rigid body part positioned to interact with said rib to allow rotational movement of said sleeve and to constrain axial movement of said sleeve.

9. The connector apparatus of claim 1 further comprising said resilient tube and said fluid transfer device, wherein said tube is a multi-lumen catheter and said tubular extension of said fluid transfer device has a matching number of lumens within a discrete tube, whereby respective ones of said catheter lumens are adapted for coupling to respective ones of said tubular extension lumens.

10. A connector apparatus in accordance with claim 1 further comprising said fluid transfer device, wherein said twist lock means comprises a pair of radially extending flanges and said fluid transfer device comprises a pair of flange receivers, whereby said pair of flanges is cooperable with said pair of flange receivers upon rotation of said body part to selectively interlockingly couple said body part and said fluid transfer device, said twist lock means further including a retention element extending radially from said body part adjacent to said pair of flanges and in a plane perpendicular to said pair of flanges, to engage with one of said pair of flange receivers, upon coupling with said transfer device to retain said connector in said interlocked position.

11. A connector apparatus in accordance with claim 10 wherein said retention element has a ramp shaped surface and at least one of said pair of flange receivers includes a projection having a ramp shaped edge positioned to latch with said retention element upon rotation of said body part.

12. A connector apparatus for coupling an end of a resilient tube about the exterior of a tubular extension of a fluid transfer device, said extension extending along a port axis and having an outer diameter d, said connector apparatus comprising:

A. said fluid transfer device,

B. a rigid tubular sleeve extending along a reference axis, said sleeve having an inner diameter $D_s$, where $D_s$ is greater than d, and C. a rigid body part disposed about said tubular sleeve and associated capture means for capturing said sleeve within said body part, whereby said sleeve is freely rotatable about said reference axis with respect to said body part, wherein said body part further includes twist lock means responsive to coaxial alignment of said port axis and said reference axis and to subsequent rotation of said body part about said reference axis and said port axis, for selectively engaging said body part to said fluid transfer device with said sleeve being coaxial with and positioned about said tubular extension, said twist lock means comprising a pair of flanges radially extending from said body part and a pair of flange receivers on said fluid transfer device, whereby said pair of flanges is cooperable with said pair of flange receivers upon rotation of said body part to selectively interlockingly couple said body part and said fluid transfer device, and wherein said twist lock means further includes a retention element extending radially from said body part adjacent to said pair of flanges and in a plane perpendicular to said pair of flanges to engage with one of said pair of flange receivers, upon coupling with said fluid transfer device to retain said body part in said interlocked position.

13. A connector apparatus in accordance with claim 12 wherein said retention element has a ramp shaped surface and at least one of said pair of flange receivers includes a projection positioned to latch with said retention element upon rotation of said body part.

* * * * *